US000001817H

United States Statutory Invention Registration [19]

[11] Reg. Number: H1,817

Hanson et al. [45] Published: Nov. 2, 1999

[54] ENZYMATIC METHODS FOR THE PREPARATION OF PRADIMICINS

[75] Inventors: Ronald L. Hanson, Morris Plains; Ramesh N. Patel, Bridgewater; Laszlo J. Szarka, East Brunswick, all of N.J.

[73] Assignee: Bristol-Myers Squibb Company, Princeton, N.J.

[21] Appl. No.: 08/734,220

[22] Filed: Oct. 21, 1996

Related U.S. Application Data

[60] Provisional application No. 60/006,158, Nov. 2, 1995.

[51] Int. Cl.[6] ..... C12P 19/56

[52] U.S. Cl. ..... 435/78

*Primary Examiner*—Charles T. Jordan
*Assistant Examiner*—Meena Chelliah
*Attorney, Agent, or Firm*—Suzanne E. Babajko

[57] ABSTRACT

Enzymatic hydrolysis and glycosidation methods for the preparation of pradimicin compounds, especially the compound BMY-28960:

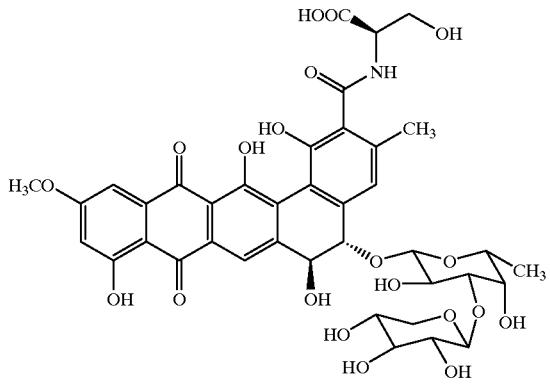

and salts thereof.

15 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENZYMATIC METHODS FOR THE PREPARATION OF PRADIMICINS

This application is based on provisional U.S. application Ser. No. 60/006,158, filed Nov. 2, 1995.

FIELD OF THE INVENTION

The present invention relates to enzymatic hydrolysis and glycosidation methods for the preparation of pradimicin compounds. The product compounds may be used as pharmacologically active entities per se, or may be used as intermediates in the preparation of other pradimicin compounds.

BACKGROUND OF THE INVENTION

Pradimicin compounds find utility as antifungal agents. Such compounds and methods for their preparation are described, for example, in U.S. Pat. Nos. 5,194,371 and 5,410,029. One such pradimicin compound, (5S-trans)-N-[[5-[[4,6-dideoxy-3-O -(beta-D-xylopyranosyl)-beta-D-galactopyranosyl]oxy]-5,6,8,13-tetrahydro-1,6,9,14-tetrahydroxy-11-methoxy-3-methyl-8,13-dioxobenzo[a]naphthacen-2-yl]carbonyl]-D-serine (referred to as "BMY-28960" or "BMS-181184"), described in the aforementioned U.S. Patents and having the following structure:

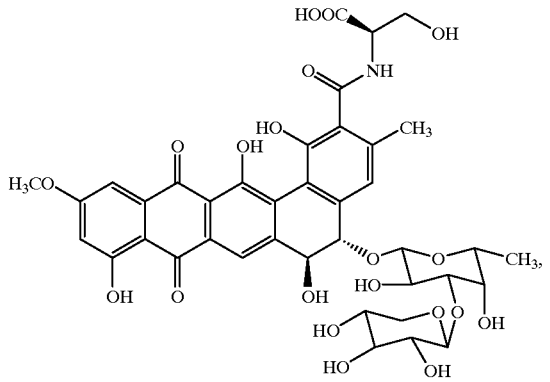

is a particularly effective antifungal agent.

In view of their activity and pharmacological utility, synthetic routes have been sought to enhance the production of pradimicin compounds.

SUMMARY OF THE INVENTION

The present invention provides enzymatic methods for the preparation of pradimicin compounds, including regioselective hydrolysis and glycosidation methods.

In particular, the present invention provides a method for converting a pradimicin compound of the following formula I or a salt thereof:

(I)

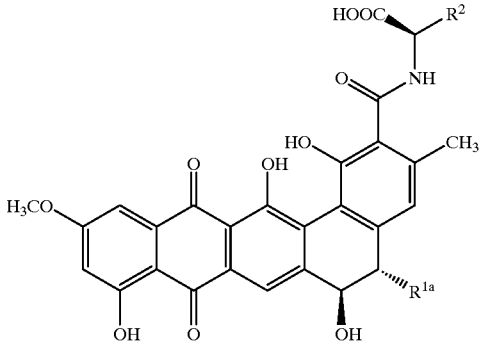

to at least one pradimicin compound of the following formula II or salt thereof:

(II)

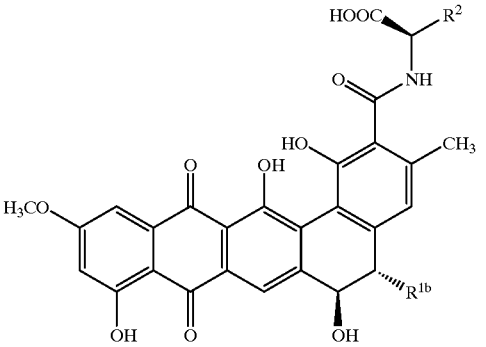

where $R^{1a}$ is a disaccharide moiety selected from the group consisting of xylosyl-fucosyl, arabinosyl-fucosyl and fucosyl-fucosyl; or a monosaccharide moiety selected from the group consisting of fucosyl, 4-deoxyfucosyl and 4-deoxy-4-fluorofucosyl;

when $R^{1a}$ is a disaccharide moiety, $R^{1b}$ is hydroxyl or a monosaccharide moiety, where said monosaccharide moiety contains the monosaccharide group of the $R^{1a}$ disaccharide moiety directly bonded to the aglycone; or, when $R^{1a}$ is a monosaccharide moiety, $R^{1b}$ is hydroxyl; and $R^2$ is hydrogen, alkyl, hydroxyalkyl or arylalkyl;

comprising the steps of contacting said pradimicin compound of the formula I or salt thereof with an enzyme or microorganism capable of catalyzing the hydrolysis of said compound I or salt thereof to form said compound II or salt thereof, and effecting said hydrolysis. The hydrolysis reaction is preferably conducted in the presence of water and/or an organic alcohol such as methanol.

The present invention also provides a method for converting a pradimicin compound of the following formula II or a salt thereof:

(II)

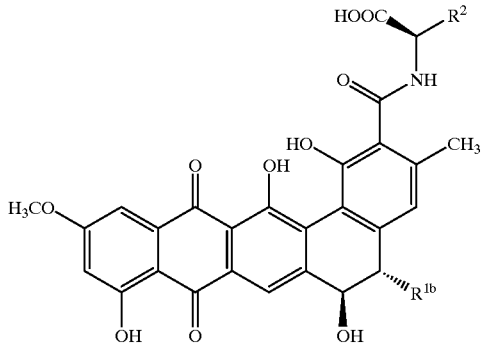

to at least one pradimicin compound of the following formula I or salt thereof:

(I)

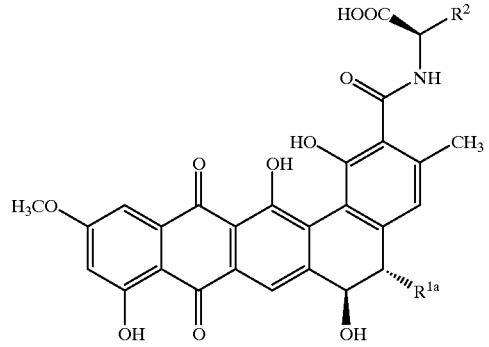

where $R^{1b}$ is hydroxyl or a monosaccharide moiety which is fucosyl;

when $R^{1b}$ is hydroxyl, $R^{1a}$ is a disaccharide moiety selected from the group consisting of xylosyl-fucosyl, arabinosyl-fucosyl and fucosyl-fucosyl, or a monosaccharide moiety selected from the group consisting of fucosyl, 4-deoxyfucosyl and 4-deoxy-4-fluorofucosyl; or, when $R^{1b}$ is a monosaccharide moiety, $R^{1a}$ is a disaccharide moiety selected from the group consisting of xylosyl-fucosyl, arabinosyl-fucosyl and fucosyl-fucosyl; and $R^2$ is hydrogen, alkyl, hydroxyalkyl or arylalkyl;

comprising the steps of contacting said pradimicin compound of the formula II or salt thereof with a sugar which is a monosaccharide selected from the group consisting of (i) fucose, 4-deoxyfucose and 4-deoxy-4-fluorofucose when $R^{1b}$ is hydroxyl, or (ii) xylose, arabinose and fucose when $R^{1b}$ is fucosyl; or a disaccharide selected from the group consisting of xylosyl-fucose, arabinosyl-fucose and fucosyl-fucose when $R^1$ is hydroxyl; or with a glycoside, such as a phenyl glycoside, of said sugar, and with an enzyme or microorganism capable of catalyzing the glycosidation of said compound II or salt thereof to form said compound I or salt thereof, with the proviso that said microorganism is not Actinomadura when $R^2$ is methyl, and effecting said glycosidation.

DETAILED DESCRIPTION OF THE INVENTION

The present invention provides an efficient method for the preparation of pradimicin compounds. One or more pradimicin compounds may be prepared simultaneously or sequentially as appropriate according to the methods of the present invention. All stereoconfigurations of the unspecified chiral centers of the compounds of the formulae I and II are contemplated in the methods of the present invention.

Definitions

The terms "enzymatic process" or "enzymatic method", as used herein, denote a process or method of the present invention employing an enzyme or microorganism. Use of "an enzyme or microorganism" in the present method includes the use of two or more, as well as a single, enzyme or microorganism.

The terms "monosaccharide moiety" and "disaccharide moiety", as used herein, denote the moieties formed by the removal of a hydrogen atom from a monosaccharide or disaccharide, respectively, whereby these moieties bond through a glycosidic (i.e., -O-) linkage. Preferred monosaccharide moieties are P-D-fucosyl groups having the following configuration:

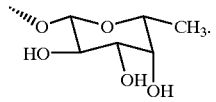

Preferred disaccharide moieties are β-D-xylosyl-β-D-fucosyl groups having the following configuration:

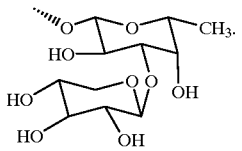

The term "glycoside", as used with respect to the aforementioned monosaccharides or disaccharides, denotes a compound wherein an organic moiety, such as a phenyl group, is bonded through a glycosidic linkage at a position corresponding to the position of a hydroxy group of said monosaccharide or disaccharide.

The term "aglycone", as used herein, denotes the part of the formulae I and II compounds not including the monosaccharide or disaccharide moieties.

The term "alkyl", as used herein, denotes straight and branched chain saturated hydrocarbon groups having 1 to 6 carbons in the normal chain. Exemplary such groups include methyl, ethyl, propyl, isopropyl, n-butyl, t-butyl, isobutyl, pentyl, hexyl, and isohexyl.

The term "hydroxyalkyl", as used herein, denotes straight and branched chain saturated hydrocarbon groups having 1 to 6 carbons in the normal chain substituted by one or more hydroxyl groups. Exemplary such groups include hydroxymethyl, hydroxyethyl, and hydroxypropyl.

The term "arylalkyl", as used herein, denotes phenylalkyl, biphenylalkyl, and naphthylalkyl, wherein the phenyl, biphenyl and naphthyl parts of these groups are unsubstituted or are substituted by up to three groups selected from hydroxyl, fluoro and/or alkyl.

The term "salt", as used herein, denotes acidic and/or basic salts formed with inorganic and/or organic acids and bases.

Starting Materials

The pradimicin compounds of the formula I or salts thereof employed as starting materials in the present hydrolysis method, or the pradimicin compounds of the formula II or salts thereof employed in the present glycosidation method, may be obtained by any suitable method such as those known in the art. Methods for the preparation of these starting materials include the fermentation and semi-synthetic methods described in U.S. Pat. Nos. 5,194,371 and 5,410,029, incorporated herein by reference, as well as those methods described in Okuyama et al., *The Journal of Antibiotics,* Vol. 46, No. 3, 500–506 (1993) and Takeuchi et al., *The Journal of Antibiotics,* Vol. XLI, No. 6, 807–811 (1988), also incorporated herein by reference.

Enzymes and Microorganisms

The enzyme or microorganism employed in the hydrolysis or glycosidation methods of the present invention may be any enzyme or microorganism capable of catalyzing, respectively, the enzymatic hydrolysis or glycosidation method described herein. The enyzmatic or microbial materials, regardless of origin or purity, may be employed in the free state or immobilized on a support such as by physical adsorption or entrapment. A given such enzyme or microorganism may be capable of both hydrolysis and glycosidation, and reaction conditions such as reaction medium, temperature, pH, relative amounts of reactants and products, etc. selected to favor the desired reaction. For example, minimizing the presence of water, and maximizing the presence of mono- or disaccharide to be added, favors the glycosidation reaction.

Exemplary microorganisms include those within the following genera: Actinomadura, Flavobacterium, Acinetobacter, Moraxella, Bacillus, Sporolactobacillus, Clostridium, Desulfotomaculum, Sporosarcina, Oscillospira, Planococcus, Lactobacillus, Kurthia, Micrococcus, Stomatococcus, Staphylococcus, Arthrobacter, Neisseria or Kingella.

Preferred microorganisms are those species within the genera Micrococcus, such as *Micrococcus luteus, Micrococcus lylae, Micrococcus varians, Micrococcus roseus, Micrococcus agilis, Micrococcus kristinae, Micrococcus nishinomiyaensis, Micrococcus sedentarius,* or *Micrococcus halobius;* Bacillus, such as *Bacillus anthracis, Bacillus thuringiensis, Bacillus mycoides, Bacillus fastidiosus, Bacillus circulans, Bacillus cereus, Bacillus insolitus, Bacillus lentus, Bacillus pantothenticus, Bacillus alcalophilus, Bacillus megaterium, Bacillus sphaericus, Bacillus marinus, Bacillus lentimorbus, Bacillus pasteurii, Bacillus azotoformans, Bacillus macquariensis, Bacillus globisporus, Bacillus laterosporus, Bacillus popilliae, Bacillus firmus, Bacillus pumilus, Bacillus subtilis, Bacillus badius, Bacillus polymyxa, Bacillus alvei, Bacillus licheniformis, Bacillus coagulans, Bacillus brevis, Bacillus stearothermophilus, Bacillus macerans, Bacillus acidocaldarius, Bacillus schlegelii,* or *Bacillus larvae;* Flavobacterium, such as *Flavobacterium acquatile, Flavobacterium breve, Flavobacterium balustinum, Flavobacterium meningosepticum, Flavobacterium odoratum, Flavobacterium multivorum,* or *Flavobacterium spiritivorum;* and, particularly, Moraxella, such as species of the subgenus Moraxella such as *Moraxella* (Moraxella) *lacunata, Moraxella* (Moraxella) *bovis, Moraxella* (Moraxella) *nonliquefaciens, Moraxella* (Moraxella) *atlantae, Moraxella* (Moraxella) *phenylpyruvica,* or *Moraxella* (Moraxella) *osloensis,* or species of the subgenus Branhamella such as *Moraxella* (Branhamella) *catarrhalis, Moraxella* (Branhamella) *caviae, Moraxella* (Branhamella) *ovis,* or *Moraxella* (Branhamella) *cuniculi.*

Especially preferred microorganisms are Moraxella sp. ATCC 55475, *Bacillus macerans* ATCC 55476, *Bacillus circulans* ATCC 55477, and Micrococcus sp. ATCC 55478. The term "ATCC" as used herein refers to the accession number of the American Type Culture Collection, 12301 Parklawn Drive, Rockville, Md. 20852, the depository for the organism referred to. These microorganisms are described in U.S. patent application Ser. No. 08/421,017, filed Apr. 12, 1995 by Ronald L. Hanson et al. (Attorney Docket No. LD64a), incorporated herein by reference. It should be understood that mutants of these microorganisms are also contemplated for use in the present invention, such as those modified by the use of chemical, physical (for example, ultraviolet radiation) or biological means (for example, by molecular biology techniques).

Exemplary enzymes for use in the present methods are hydrolases, particularly glycosidases or glycanases. Preferred enzymes include those derived from microorganisms, particularly those microorganisms described above. Such enzymes may be isolated, for example, by extraction and purification methods.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. *Escherichia coli,* modified to contain a gene or genes for expressing one or more enzymes capable of catalysis as described herein.

Where one or more microorganisms are employed, the enzymatic hydrolysis or glycosidation methods of the present invention may be carried out subsequent to the fermentation of the microorganism (two-stage fermentation and hydrolysis or glycosidation), or concurrently therewith, that is, in the latter case, by in situ fermentation and hydrolysis or glycosidation (single-stage fermentation and hydrolysis or glycosidation).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, xylan and the like; salts of organic acids such as sodium acetate, sodium citrate, and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements may include magnesium, manganese, calcium, cobalt, molybdenum, copper, nickel, iron, sodium and potassium salts. Phosphates may also be added in trace, or preferably, greater than trace amounts.

The medium employed may include more than one carbon or nitrogen source or other nutrient.

Preferred media for growth include aqueous media, such as those described in the Examples herein.

The agitation and aeration of the reaction mixture affects the amount of oxygen available during growth. An agitation range from 100 to 250 RPM is preferred; aeration of about 1 to 10 volumes of air per volume of media per minute is preferred.

For growth of the microorganisms and/or hydrolysis according to the methods of the present invention, the pH of the medium is preferably from about 4 to about 8.5, and the temperature is preferably from about 24° C. to about 37° C. Hydrolysis may, for example, be carried out in vitro over time periods such as 1 to 72 hours, or preferably until the yield of desired product is maximized. It is also preferred to employ an aqueous liquid as the hydrolysis reaction medium, although an organic liquid, or a miscible or immiscible (biphasic) organic/aqueous liquid mixture may also be employed. It is preferred to employ 0.05 to 1 weight % of the pradimicin compound starting material based on the combined weight of starting material and hydrolysis reaction medium.

For growth of the microorganisms and/or glycosidation according to the methods of the present invention, the pH of the medium is preferably from about 4 to about 8.5, and the temperature is preferably from about 20° C. to about 40° C. Glycosidation may, for example, be carried out in vitro over time periods such as 1 to 72 hours, or preferably until the yield of desired product is maximized. It is also preferred to employ an aqueous liquid as the glycosidation reaction medium, although an organic liquid, or a miscible or immiscible (biphasic) organic/aqueous liquid mixture may also be employed. It is preferred to employ 0.05 to 1 weight % of the pradimicin compound starting material, and 0.1 to 5 weight % of the mono- or disaccharide starting material, based on the combined weight of starting materials and glycosidation reaction medium.

The amount of enzyme or microorganism employed relative to the starting material is selected to allow catalysis of the enzymatic hydrolysis or glycosidation methods of the present invention.

Where it is desired to ultimately prepare a compound where $R^{1a}$ is a disaccharide moiety and the starting compound contains an $R^{1b}$ group which is hydroxyl, the disaccharide moiety may be formed by sequential addition of the monosaccharides forming the desired disaccharide moiety.

Solvates such as hydrates of reactants or products may be employed or prepared as appropriate in any of the methods of the present invention.

Separation

The pradimicin products of the methods of the present invention may be isolated and purified, for example, by methods such as extraction, distillation, crystallization, and column chromatography.

Utility

Pradimicin compounds of the formulae I and II where $R^{1a}$ or $R^{1b}$ is a monosaccharide or disaccharide moiety, prepared by the present methods, may be employed as antifungal agents per se. In this regard, see U.S. Pat. Nos. 5,194,371 and 5,410,029, and Okuyama et al., *The Journal of Antibiotics,* Vol. 46, No. 3., 500–506 (1993), all incorporated herein by reference.

Compounds of the formulae I and II prepared by the present methods may also, if desired, be employed to prepare other pradimicin compounds within these formulae. For example, where the present hydrolysis method yields a compound where $R^{1b}$ is hydroxyl, a desired mono- or disaccharide moiety may be added at the corresponding position either by the present glycosidation method or other suitable method.

Preferred Compounds

Compounds prepared by or employed in the present methods preferably contain one or more, most preferably all, of the following groups:

$R^{1a}$ or $R^{1b}$ which is hydroxyl or fucosyl or, most preferably for $R^{1a}$, xylosyl-fucosyl; and $R^2$ which is methyl or, most preferably, hydroxymethyl.

Preferred salts are ammonium or alkali metal salts, such as potassium or, especially, sodium salts.

The compound BMY-28960 or a salt thereof is most preferably ultimately prepared by the methods described herein.

The present invention is further described by the following Examples, which are illustrative only and are in no way intended to limit the scope of the present claims.

EXAMPLE 1

GROWTH OF CELLS

Moraxella sp. ATCC 55475 was isolated from soil as described in U.S. patent application No. 08/421,017, filed Apr. 12, 1995 by Ronald L. Hanson et al. (Attorney Docket No. LD64a). This strain was grown in shake flasks at 28° C. on aqueous media containing by weight, at pH 7: 2% glycerol, 0.2% tryptone, 0.2% yeast extract, 0.1% $K_2HPO_4$, 0.1% $KH_2PO_4$, 0.02% $MgSO_4 \cdot 7H_2O$, 0.001% NaCl, 0.001% $FeSO_4 \cdot 7\ H_2O$, and 0.001% $MnSO_4 \cdot 4H_2O$. A 1 ml vial was used to inoculate 100 ml medium. After 4 days, 15 ml of this culture were used to inoculate 1 L medium in a 4 L Erlenmeyer flask. After 3 days, the 1 L culture was used to inoculate a 15 L fermenter and grown at 28° C. on aqueous media containing by weight: 2% glycerol, 0.2% tryptone, 0.2% yeast extract, 0.43% $K_2HPO_4$, 0.02% $MgSO_4 \cdot 7H_2O$, 0.001% NaCl, 0.001% $FeSO_4 \cdot 7H_2O$, 0.001% $MnSO_4 \cdot 4H_2O$ and 0.025% UCON LB625 antifoam. After 75 hours, 147.5 g cells were harvested by centrifugation and stored frozen. Cells were washed with 50 mM potassium phosphate pH 7 buffer before use and centrifuged again.

EXAMPLE 2

HYDROLYSIS USING CELLS 20 mg of the following pradimicin compound designated Pradimicin X:

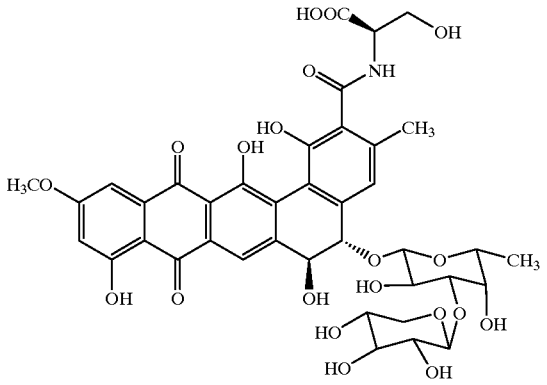

-continued (containing the following alanine analog as a minor componant:

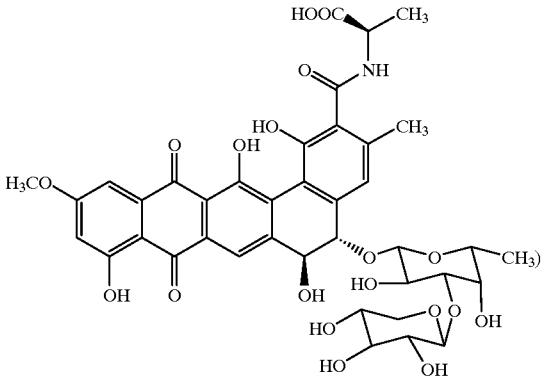

in 20 ml water adjusted to pH 8, 2 ml 1 M potassium phosphate buffer pH 8, 18 ml water and 4 g Moraxella sp. ATCC 55475 cells obtained as in Example 1 (washed with 50 mM potassium phosphate buffer pH 8) were stirred at room temperature (23–24° C.) for 24 hours.

A sample of the product obtained was analyzed by LC/MS, which showed that the following compounds designated Pradimicin Y and Pradimicin Z were obtained which, compared with the starting Pradimicin X, were missing one or both sugars:

Pradimicin Y:

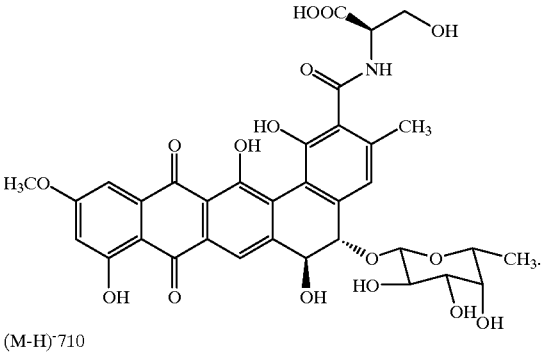

$(M-H)^-$710

Instrument: Finnigan MAT TSQ 7000

Ionization: Electrospray, negative ions

Pradimicin Z:

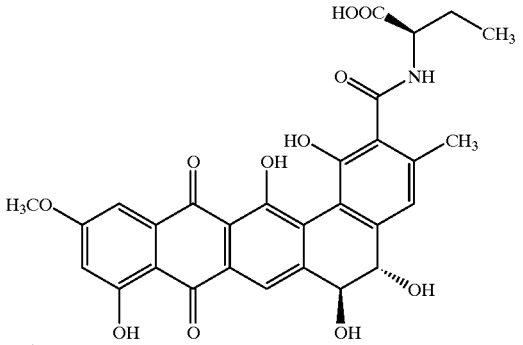

$(M-H)^-$564

Analogs of the "alanine analog" shown above, also missing one or both sugars, were also obtained as follows:

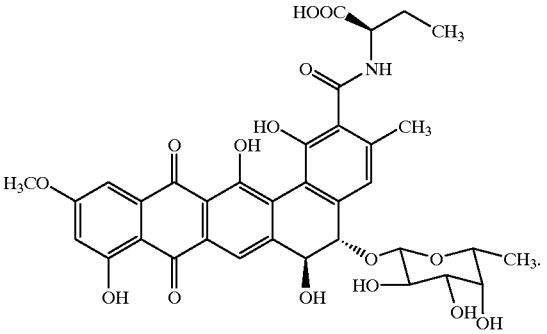

$(M-H)^-$694

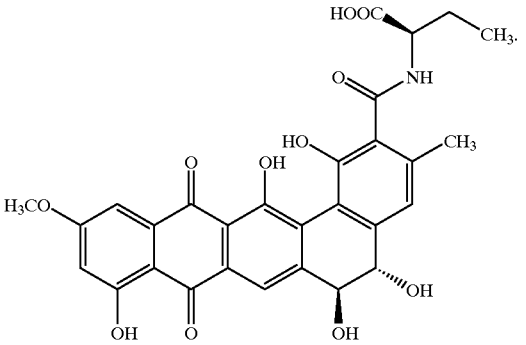

$(M-H)^-$549

EXAMPLE 3

HYDROLYSIS USING CELL FRACTIONS

Moraxella sp. ATCC 55475 cells obtained as in Example 1 (7 g washed with 50 mM potassium phosphate buffer pH 8) were suspended in 35 ml 50 mM potassium phosphate buffer pH 8. A 2 ml portion of the suspension was saved, and the remainder was disrupted by sonication for 2 two-minute intervals. The homogenate was centrifuged at 11,915xg for 10 minutes and the pellet was discarded. 5 ml of the supernatant was centrifuged at 101,000xg for 30 minutes. The pellet was resuspended in 5 ml 50 mM potassium phosphate buffer pH 8. The 2 ml cell suspension, 2 ml of the 101,000xg supernatant, and 2 ml of the 101,000xg pellet fractions were each incubated with 2 ml 50 mM potassium phosphate buffer pH 8 containing 2 mg Pradimicin X. The cell suspensions were incubated in tubes at 28° C. and 12 RPM on a rotating rack. The other samples were incubated in a water bath at 30° C. The samples were analyzed by HPLC as described below. The results which were obtained are described in the following Table 1.

TABLE 1

| Sample | Time (hrs) | Pradimicin Z (%) | Pradimicin Y (%) | Pradimicin X (%) | Recovery (%) |
|---|---|---|---|---|---|
| Cells | 16 | 0 | 23.1 | 43.1 | 66.2 |
| Cells | 43 | 10.2 | 25.6 | 34.9 | 70.7 |
| Cells | 65 | 13.2 | 28.4 | 33.4 | 75.0 |
| 101,00 × g supernatant | 16 | 0 | 12.4 | 80.8 | 93.2 |
| 101,000 × g supernatant | 43 | 5.6 | 14.7 | 51.5 | 71.8 |

TABLE 1-continued

| Sample | Time (hrs) | Pradimicin Z (%) | Pradimicin Y (%) | Pradimicin X (%) | Recovery (%) |
|---|---|---|---|---|---|
| 101,000 × g supernatant | 65 | 14.6 | 20.5 | 60.8 | 96.0 |
| 101,000 × g pellet | 16 | 0 | 28 | 32.0 | 60.1 |
| 101,000 × g pellet | 43 | 6.9 | 21.4 | 22.3 | 50.6 |
| 101,000 × g pellet | 65 | 10.7 | 24.3 | 22.7 | 57.8 |

HPLC Analysis

Sample preparation: 0.65 ml acetonitrile was 10 added to 0.65 ml sample and the mixture was vortexed for 5 minutes, then microfuged at 15850xg for 5 minutes. 1 ml supernatant was dried at 50° C. under a nitrogen stream. The residue was dissolved in 1 ml water and microfuged again before HPLC analysis.

Column: Waters Novapak C18 4 $\mu$, 3.9 mm×150 mm
Temperature: 40° C.
Detection wavelength: 300 nm
Flow rate: 1 ml/min
Mobile phase:
0–2 minutes: 100% 20 mm ammonium acetate
2–25 minutes: linear gradient of 0 to 20% acetonitrile, 100 to 80% 20 mM ammonium acetate
25–30 minutes: 100% 20 mM ammonium acetate Calibration: Standards were used for Pradimicin X, Pradimicin Y (dexylosyl), and Pradimicin Z (aglycone) to determine retention times (20.6, 18.9 and 15.7 minutes, respectively). For calculation of yields, the initially added Pradimicin X was taken as 100% and the product amounts were based on area % of the initial pradimicin peak (sugar removal would not be expected to affect absorbance at 300 nm). The % recovery is calculated as the sum of peak areas for Pradimicins X, Y and Z in the product relative to the area of the initial Pradimicin X peak.

EXAMPLE 4

GLYCOSIDATION USING CELLS

Pradimicin Z:

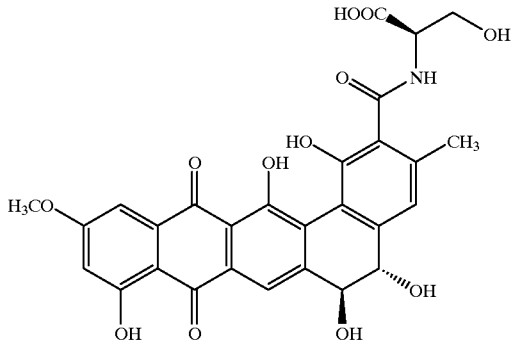

in the amount of 20 mg, and 200 mg phenyl xylosyl-fucoside are added to 20 ml 50 mM potassium phosphate buffer pH 8 containing 4 g Moraxella sp. ATCC 55475 cells which are obtained as in Example 1 (washed with 50 mM potassium phosphate buffer pH 8). After stirring the mixture at room temperature for 24 hours, the product which is obtained by glycosidation (in particular, transglycosidation) includes Pradimicin X (i.e., BMY-28960):

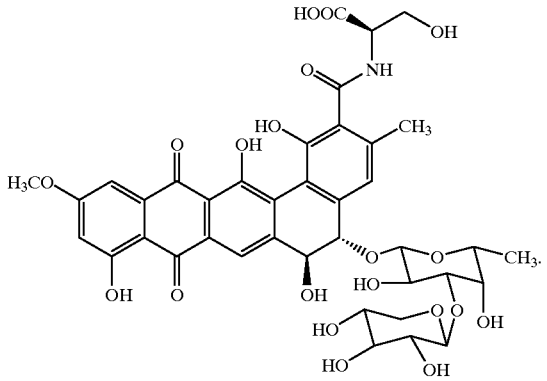

What is claimed is:

1. A method for converting a pradimicin compound of the following formula I or a salt thereof:

(I)

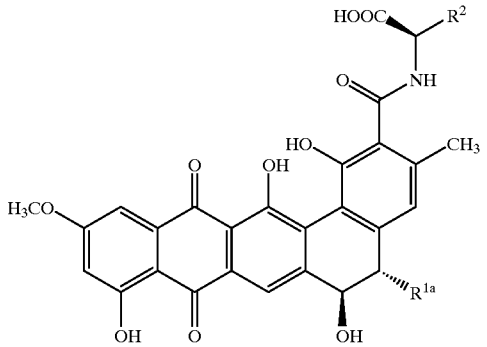

to at least one pradimicin compound of the following formula II or salt thereof:

(II)

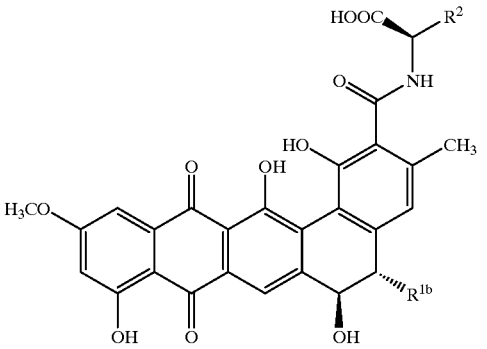

where $R^{1a}$ is a disaccharide moiety selected from the group consisting of xylosyl-fucosyl, arabinosyl-fucosyl and fucosyl-fucosyl; or a monosaccharide moiety selected from the group consisting of fucosyl, 4-deoxyfucosyl and 4-deoxy-4-fluorofucosyl;

when $R^{1a}$ is a disaccharide moiety, $R^{1b}$ is hydroxyl or a monosaccharide moiety, where said monosaccharide moiety contains the monosaccharide group of the $R^{1a}$ disaccharide moiety directly bonded to the aglycone; or, when $R^{1a}$ is a monosaccharide moiety, $R^{1b}$ is hydroxyl; and $R^2$ is hydrogen, alkyl, hydroxyalkyl or arylalkyl;

comprising the steps of contacting said pradimicin compound of the formula I or salt thereof with an enzyme or microorganism capable of catalyzing the hydrolysis of said compound I or salt thereof to form said compound II or salt thereof, and effecting said hydrolysis.

2. The method of claim 1, wherein $R^{1a}$ is fucosyl or xylosyl-fucosyl;

$R^{1b}$ is hydroxyl or fucosyl; and $R^2$ is methyl or hydroxymethyl.

3. The method of claim 2, wherein the compound having the following structure, or a salt thereof:

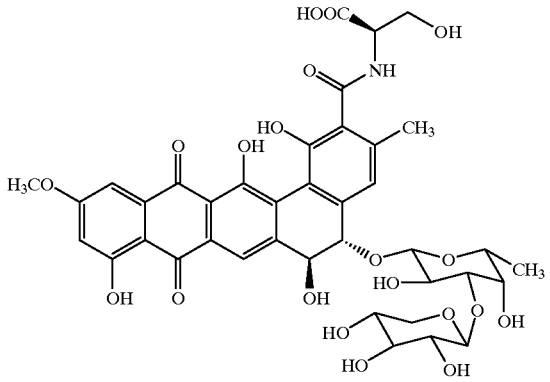

is employed, and at least one of the compounds having the following structures, or salts thereof, are prepared:

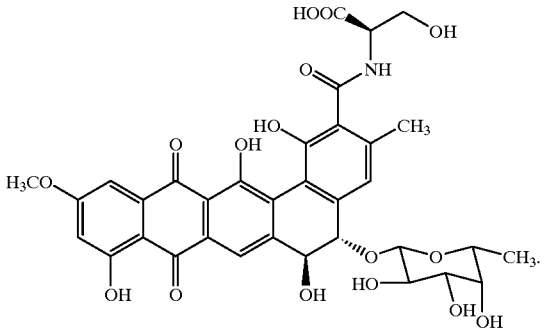

or

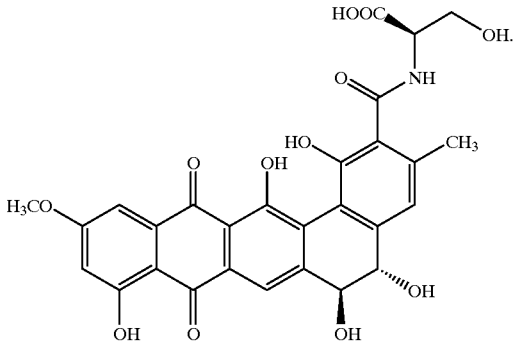

4. The method of claim 2, wherein the compound having the following structure, or a salt thereof:

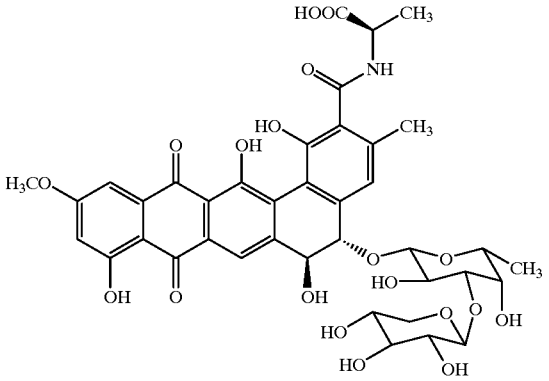

is employed, and at least one of the compounds having the following structures, or salts thereof, are prepared:

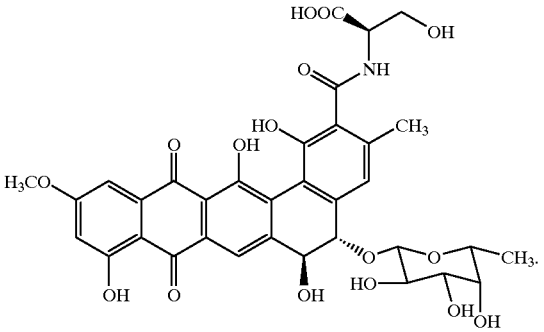

or

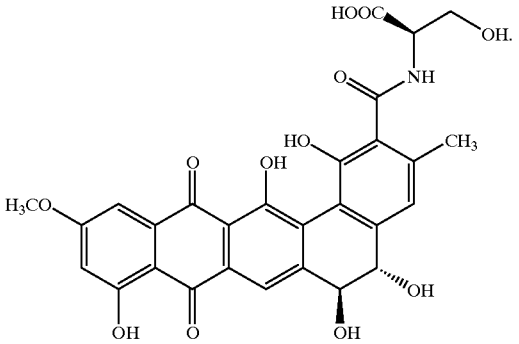

5. The method of claim 1, wherein a microorganism is employed which belongs to one of the following genera: Actinomadura, Flavobacterium, Acinetobacter, Moraxella, Bacillus, Sporolactobacillus, Clostridium, Desulfotomaculum, Sporosarcina, Oscillospira, Planococcus, Lactobacillus, Kurthia, Micrococcus, Stomatococcus, Staphylococcus, Arthrobacter, Neisseria or Kingella, or wherein an enzyme derived from a microorganism belonging to one of said genera is employed.

6. The method of claim 5, wherein a microorganism is employed which belongs to the genus Flavobacterium, Moraxella, Micrococcus or Bacillus, or wherein an enzyme derived from a microorganism belonging to one of said genera is employed.

7. The method of claim 3, wherein a microorganism is employed which belongs to the genus Flavobacterium, Moraxella, Micrococcus or Bacillus, or wherein an enzyme derived from a microorganism belonging to one of said genera is employed.

8. The method of claim 6, wherein said microorganism, or the microorganism from which said enzyme is derived, is Moraxella sp. ATCC 55475.

9. A method for converting a pradimicin compound of the following formula II or a salt thereof:

(II)

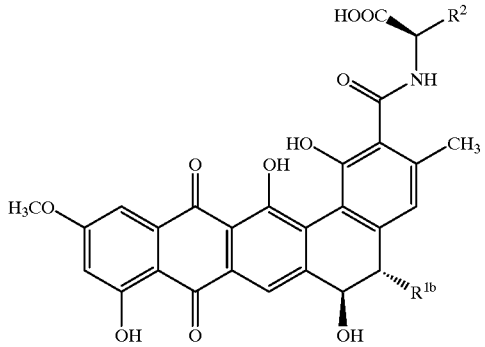

to at least one pradimicin compound of the following formula I or salt thereof:

(I)

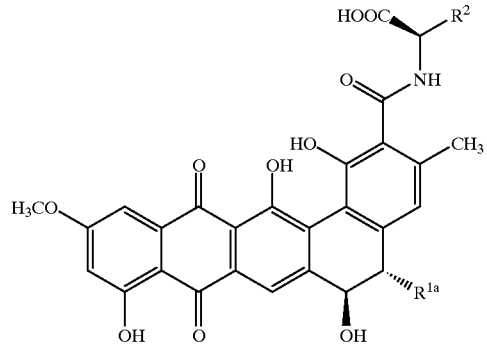

where $R^{1b}$ is hydroxyl or a monosacharide moiety which is fucosyl;

when $R^{1b}$ is hydroxyl, $R^{1a}$ is a disaccharide moiety selected from the group consisting of xylosyl-fucosyl, arabinosyl-fucosyl and fucosyl-fucosyl, or a monosaccharide moiety selected from the group consisting of fucosyl, 4-deoxyfucosyl and 4-deoxy-4-fluorofucosyl; or, when $R^{1b}$ is a monosaccharide moiety, $R^{1a}$ is a disaccharide moiety selected from the group consisting of xylosyl-fucosyl, arabinosyl-fucosyl and fucosyl-fucosyl; and $R^2$ is hydrogen, alkyl, hydroxyalkyl or arylalkyl;

comprising the steps of contacting said pradimicin compound of the formula II or salt thereof with a sugar which is a monosaccharide selected from the group consisting of (i) fucose, 4-deoxyfucose and 4-deoxy-4-fluorofucose when $R^{1b}$ is hydroxyl, or (ii) xylose, arabinose and fucose when $R^{1b}$ is fucosyl; or a disaccharide selected from the group consisting of xylosyl-fucose, arabinosyl-fucose and fucosyl-fucose when $R^{1b}$ is hydroxyl; or with a glycoside of said sugar, and with an enzyme or microorganism capable of catalyzing the glycosidation of said compound II or salt thereof to form said compound I or salt thereof, with the proviso that said microorganism is not Actinomadura when $R^2$ is methyl, and effecting said glycosidation.

10. The method of claim 9, wherein $R^{1a}$ is fucosyl or xylosyl-fucosyl;

$R^{1b}$ is hydroxyl or fucosyl; and $R^2$ is methyl or hydroxymethyl.

11. The method of claim 10, wherein the compound BMY-28960 having the following structure:

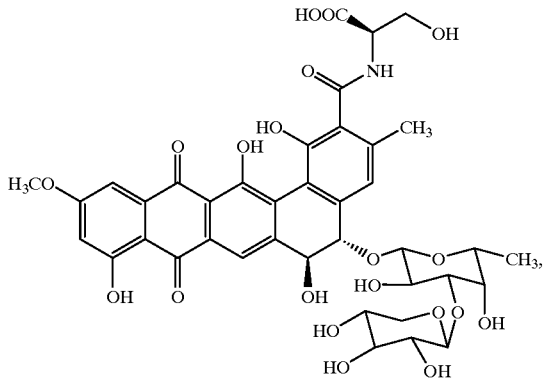

or a salt thereof, is prepared.

12. The method of claim 9, wherein a microorganism is employed which belongs to one of the following genera: Actinomadura, Flavobacterium, Acinetobacter, Moraxella, Bacillus, Sporolactobacillus, Clostridium, Desulfotomaculum, Sporosarcina, Oscillospira, Planococcus, Lactobacillus, Kurthia, Micrococcus, Stomatococcus, Staphylococcus, Arthrobacter, Neisseria or Kingella, or wherein an enzyme derived from a microorganism belonging to one of said genera is employed.

13. The method of claim 12, wherein a microorganism is employed which belongs to the genus Flavobacterium, Moraxella, Micrococcus or Bacillus, or wherein an enzyme derived from a microorganism belonging to one of said genera is employed.

14. The method of claim 11, wherein a microorganism is employed which belongs to the genus Flavobacterium, Moraxella, Micrococcus or Bacillus, or wherein an enzyme derived from a microorganism belonging to one of said genera is employed.

15. The method of claim 13, wherein said microorganism, or the microorganism from which said enzyme is derived, is Moraxella sp. ATCC 55475.

* * * * *